United States Patent [19]

Lenkei

[11] Patent Number: 4,597,767
[45] Date of Patent: Jul. 1, 1986

[54] SPLIT LEAFLET HEART VALVE

[76] Inventor: Andrew Lenkei, 79 Mapleleaf Dr., Williamsville, N.Y. 14221

[21] Appl. No.: 438,571

[22] Filed: Dec. 15, 1982

[51] Int. Cl.$^4$ .......................... A61F 2/24; F16K 15/00
[52] U.S. Cl. ........................................ 623/2; 137/512; 137/527
[58] Field of Search ...................... 3/1.5; 137/512, 527, 137/527.8; 623/2

[56] References Cited

U.S. PATENT DOCUMENTS

| 3,127,148 | 3/1964 | Collar | 137/527 X |
| 3,546,711 | 12/1970 | Bokros | 137/527.8 X |
| 4,114,202 | 9/1978 | Roy et al. | 3/1.5 |
| 4,178,638 | 12/1979 | Meyer | 3/1.5 |
| 4,274,437 | 6/1981 | Watts | 3/1.5 |
| 4,276,658 | 7/1981 | Hanson et al. | 3/1.5 |

Primary Examiner—Ronald L. Frinks
Attorney, Agent, or Firm—A. A. Saffitz

[57] ABSTRACT

A check valve for cardiac surgery and the like has a hollow valve body supporting spring biased split leaflets hinged for swinging movement from the base thereof between normally closed position and open position wherein the leaflets form a continuation of one end of the hollow annular valve body. Out turned edges of the separable spring biased split leaflets are in sealed engagement with a seat on the valve body and terminate in longitudinal edges which are in sealed engagement with adjacent leaflet sealing edges in the normally closed position. Said longitudinal out turned edges provide braking action to slow the closing velocity of te leaflets during the closing portion of their cycle. Said longitudinal out turned edges are shaped to provide a cushioning effect at the instant of closure due to their resiliency and springiness thereby minimizing closing impact and blood cell damage.

5 Claims, 6 Drawing Figures

SPLIT LEAFLET HEART VALVE

This invention relates to check type valves and more particularly to novel and improved check valves for cardiac surgery of the Mitral, Aortic and similar valves.

One of the common ailments of the human heart is the failure of one or more valves in the heart. Cardiac surgery is now a common medical procedure and a variety of forms of valves has heretofore been used to replace defective Mitral or Aortic valves in the human heart such as for instance the ball and cage type, center hinged disk type, porcine xenografts, and human tissue valves. Difficulties and problems attend the presently known artificial heart valves. The ball and cage valves, the center hinged disk valves, and the ocluder disk valves damage blood cells due to severe impact of the ball and disk onto their respective seats at the instant of closure, thus crushing blood cells and other organic matter in between the sealing surfaces.

Tissue valves on the other hand do not damage blood cells but they have limited durability, resulting in valve disfunction in a relatively short period of time. The glutaraldehyde stabilized porcine xenografts are excellent however long term function is limited mainly due to leaflet calcification. In general prior artificial heart valves have fallen short of achieving the performance, function and durability of the human heart valve.

Accordingly it is an object of this invention to provide a compact, lightweight, durable and reliable check valve for cardiac surgery and the like, which will substantially imitate the functioning, performance and durability of the human heart valve for either in the Mitral or Aortic positions.

It is an other object of this invention to provide a novel and improved check valve for movement between a normally closed and open position, having highly sensitive, longitudinally split leaflet members. Said leaflet members being gently urged by spring means toward the closed position while being movably attached to the main valve body by cylindrical fastening means made from pure silver, or teflon or pyrolitic carbon or a combination thereof materials which are biocompatible solid lubricants.

In accordance with the present invention I provide a check valve including a hollow valve body adapted for mounting in a fluid flow passage which supports a split leaflet having separable portions supported at the base thereof for swinging movement, the separable leaflet portions are generally arcuate in cross section and have *outturned* sealing edges from the elongated outer edges of the leaflet and seal against a seat on the valve body and the adjacent leaflet's sealing edges in the closed position. The separable leaflet portions pivot away from one another to provide, with the out turned edges a stream lined inner flow path, these wall surfaces form longitudinal continuation of the stream lined hollow annular valve body for smooth laminar flow therethrough. Said pivot means consisting of biocompatible solid lubricant materials such as medical grade silver, medical grade teflon pyrolitic carbon or a combination thereof. Said pivot means consisting of a loosely fitting hole thru said leaflets about said pivot means, to allow ample clearance for blood cell passage. It is another object of this invention.

It is another object of this invention to provide a check valve including a hollow valve body supporting split leaflets urged towards the closed position by spring means in order to substantially eliminate the closing shock characteristic of current mechanical heart valves. Natural human and porcine valves are in the closed position when pressure on both sides are equal. It requires a small but definite overpressure on the inflow side to start opening the tissue valves. Gradual increase in the pressure on the inflow side increases the amount the leaflets open until such time that the leaflets are fully open at full pressure. It is an other object of this invention to simulate the smooth opening and closing action of natural valves by the use of spring biased leaflets.

It is another object of this invention to provide a novel and improved check value for controlled movement between normally closed and open positions, having highly sensitive sensitive foil leaflets with outturned sealing edges of adaquate size to offer substantial resistance to motion especially during the closing cycle of the leaflets so that the instant of contact between the leaflet sealing surfaces is gentle and free from impact stress which may damage blood cells. These outturned sealing edges being made of thin foil or the like to provide a cushioning effect at the instant of closure due to the resiliency and springiness of of their material and configuration thereby minimizing contact stress between the adjacent sealing edges.

The above and other objects, advantages and capbilities of the present invention will become more readily understood from a consideration of a detailed description in conjuction with the accompanying drawings in which:

FIG. 1. is a vertical cross sectional view of the valve having a suture ring secured thereto, the separable foil leaflets are being shown in full lines in the closed position and in dotted lines in the open position.

FIG. 5 shows flat sealing edges 9 and 10 configurations.

FIG. 6 shows curved sealing edges 9 and 10 configurations.

Figure 4:
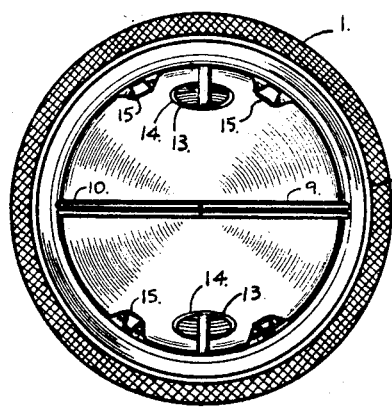
FIG. 4 is an axial view of the outflow end of the closed valve.
Figure 1:
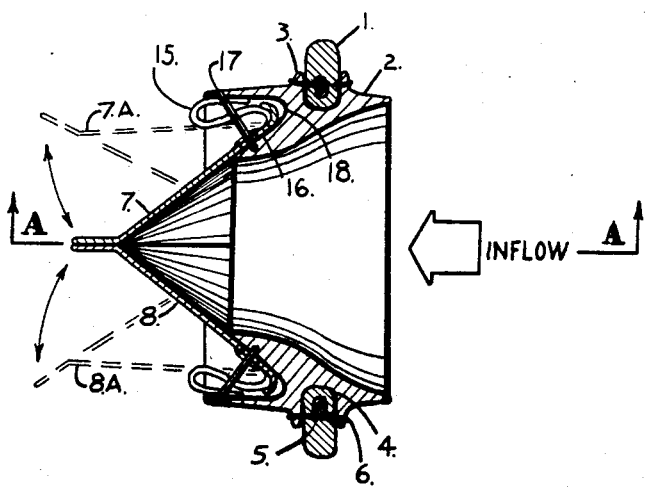

With reference to a check valve as shown on FIG. 1, such a valve is to be mounted in the Mitral, Aortic or similar positions in the heart and secured there by sutures passing thru the suture ring 1 and the heart wall. Apart from the Mitral and Aortic positions in the left ventricle of the heart, it is understood that it is also suitable for valve replacement in the right ventricle of the heart as well as for use in aritficial hearts, left ventricle assist devices, blood pumps and the like.

The check valve as shown on FIG. 1 for installation in a heart has an annular hollow valve body 2 provided with a peripheral flanged portion 3 against which a suitable suture ring 1 is secured. The annular hollow valve body 2 is also provided with a recessed groove 4 to contain seat said suture ring 1. The suture ring 1 is secured against said flanged portion 3 and is extending radially outward from said valve housing 2. Said suture ring 1 is held in place by a resilient band 5 as well as by sutures 6 securing said suture ring 1 to said flanged portion 3.

The hollow annular housing 2 supports or provides a base for a split leaflet type structure composed of two or more separable leaflets 7 and 8 which extend from one side of said housing 2 in the direction of flow and function to regulate the fluid flow therethrough, permitting flow in one direction only with negligible back flow or leakage. The leaflets 7 and 8 move between normally closed position as shown in solid lines and open position 7A and 8A indicated with dashed lines. There may be a number of leaflets mounted on a single housing 2. However two or three leaflets forming bicuspid or tricuspid valves are the only ones that are significant in heart valve replacement surgery.

Figure 3:
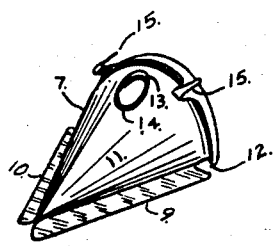
FIG. 3 is a perspective view of one of the separable leaflets shown on FIG. 1 and 2.

The separable leaflets 7 and 8 are best shown on FIG. 3, said leaflets 7 and 8 have outturned edges or sealing lips 9 and 10 on a half conical body 11 having a curved edge 12 on its base to stiffen and reinforce said conical body 11. Said half conical body 11 having a circular or elliptical opening 13 at close proximity to said curved edge 12 and located at the mid point of the distance between edges 9 and 10 Said opening 13 having a reinforcing edge 14 on its circumference. A pair of leaf springs 15 located at the free side of the said curved edge 12 and are distributed one on each side of the said opening 13 as shown in FIG. 3 and reference is made to FIG. 1 which shows the placement of pins 17 through the oversized openings 13 with the ends of pin 17 being retained between the opposite inner walls of seating groove 18. Note the S shaped configuration in cross section of the leaf spring 15 is shown at the top portion and at the bottom portion of FIG. 1.

The arcuate bottom edge portion of the leaflet 7 and 8 diverges outwardly from the apex to fit against the inner divergent wall of groove 18 and the very end of the bottom edge of the leaflet is hook shaped to conform with the curved bottom of groove 18 while the S cross section of leaf spring 15 nests against the curved bottom hook.

Figure 2:
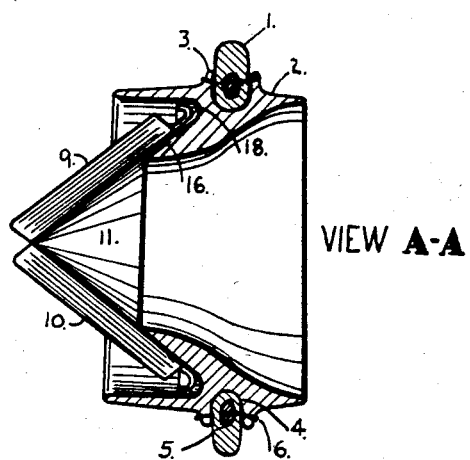
FIG. 2 is a sectional view taken along the line A—A of FIG. 1 passing between the longitudinal sealing edges of the adjacent leaflets.
Figure 5:
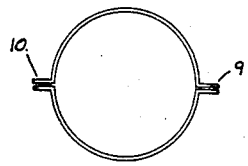
FIG. 5 and FIG. 6 show cross sectional views of the closed leaflets at right angle to the longitudinal axis of the valve and the different sealing edge 9 and 10 configurations.
Figure 6:
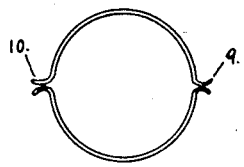

The close fitting relationship of the bottom hook portion of the leaflet within groove 18 in the edge mating region at edges 9 and 10 formed as rectangular projections or sealing lips extending perpendicularly from the leaflets 7 and 8 is shown in FIG. 2 which is a sectional view along line A—A of FIG. 1.

As described above the separable leaflet portions 7 and 8 will normally contact each other centrally and longitudinally of the valve housing 2, with the rectangular sealing lips 9 and 10 in sealed engagement with one another and the curved edge 12 in sealed engagement with nozzle surface 16.

Each separable leaflet portion 7 and 8 is loosely held in position by one or more pins 17 which are anchored into the walls of the sealing groove 18.

As explained above in the description of FIGS. 1 and 2, and in view of the specific illustration of seating groove 18 in these FIGS., it is clear that groove 18 has a generally V cross section with a rounded bottom at the lower apex of the V, the one inner wall which fits against the lower bottom curved portion of leaflet portions 7 and 8 being divergent to accommodate the specific curvature of the conical sections defined by these leaflet portions, 7 and 8, while the bottom of the V section is rounded to closely accommodate the bottom hook edge of each of these leaflet portions, the outer distal edge within the groove 18 remote from the nesting edge of the leaflet being straight in the fashion of a cylindricl straight edge and serving to retain the leaf springs 15 and with pin 17 in each oversized opening 13. Effectively, the pin 17 within oversized opening 13 serves as the loose pivot for opening and closing movement of foil leaflet portions 7 and 8, the leaf springs 15 at bottom of the leaflet portions 7 and 8, pins 17 and openings 13 all lying within the divergent inner wall and straight inner wall of groove 18 to provide the essential valve seating and pivoting means for the invention.

The opening 13 is oversized so that when the leaflet 7 and 8 is assembled into groove 18 the retaining pin 17 retains but does not interfere with leaflet motion. The loose fit permits the opening and closing movements about pin 17. The leaflets 7 an 8 are located 180° apart in Mitral or bicuspid valves and 120° apart in Aortic or tricuspid valves. (The tricuspid valves having three leaflets.)

A preferred construction is to form each separable leaflet from stainless steel foil, titanium foil or pyrolitic carbon and the like. The leaflets may be composed of various materials which will insure smooth positive sealing action and biocompatibility. When closed the separable leaflets 7 and 8 will pivot under pressure away from each other through a relatively small angle where the inner surfaces of the leaflets will be generally parallel to one another and the longitudinal axis of the valve housing 2. As the flow through the valve decreases springs 15 gently urge the leaflets toward the closed position. Such positive closing action imitates natural tissue valve action where the leaflets tend to close when pressures on both side of the valve are equal.

It is therefore to be understood that various modifications and changes may be made in the specific construction and arrangement of parts comprising the preferred and modified forms of the present invention without departing from the spirit thereof.

I claim:

1. In a heart valve comprising a hollow annular valve body supporting a plurality of interfitting conically shaped identical leaflet portions each having equiangular arcs to form at least a two cusp valve which is seated for opening and closing movement at the base of each of said leaflet portions where said valve body supports leaflet portions, that improvement comprising:
   a valve seating means formed as a recessed circumferential groove of V section in said valve body at the upper edge thereof which constitutes the sole seating groove within which each leaflet is mounted for pivotal opening and closing movement;
   the V section of said groove being formed with one divergent inner surface along which a divergent conical base portion of each leaflet conforms, being formed with a rounded bottom portion at the bottom apex and being formed with a straight distal inner wall portion adapted to retain retaining, pivoting and leaflet spring means which also lie wholly within the groove;
   each of said leaflet portions being provided with at least one oversized opening at the base to accommodate a pin and further being formed as a hook at the bottom edge to conform to the curved bottom of the groove;
   a pin in each opening held at its ends between the inner divergent wall and the inner distal straight wall to serve as a pivot for the opening and closing movement of each of the leaflets with respect to the adjacent leaflet;

each of said leaflet portions composed of foil selected from the class consisting of stainless steel, pyrolytic carbon and titanium;

each of said leaflet portions having projecting rectangular lip portions which interfit against adjacent leaflet portions to lie flat against each other; and a plurality of leaf spring means lying wholly within said groove nesting against the hook edge of said leaflet portions on opposite sides of said pin and oversized openings and retained by the straight distal wall of said groove.

2. A valve as claimed in claim 1 wherein each said leaflet portion is formed of stainless steel foil.

3. A valve as claimed in claim 2 wherein said rectangular lip portions are curved upwardly away from each other.

4. A valve as claimed in claim 2 wherein said hollow annular body is further provided with a further recessed groove and a suture ring fitting into and seating said further groove to adapt the sewing and fastening attachment of said valve to a blood vessel.

5. A valve as claimed in claim 2 wherein said oversized opening is circular.

* * * * *